(12) United States Patent
Vitello (10) Patent No.: US 8,864,708 B1
(45) Date of Patent: Oct. 21, 2014

(54) TAMPER INDICATING CLOSURE ASSEMBLY

(75) Inventor: Jonathan Vitello, Fort Lauderdale, FL (US)

(73) Assignee: Medical Device Engineering, LLC., Pompano Beach, FL (US)

( * ) Notice: Subject to any disclaimer, the term of this patent is extended or adjusted under 35 U.S.C. 154(b) by 133 days.

(21) Appl. No.: 13/310,445

(22) Filed: Dec. 2, 2011

Related U.S. Application Data (60) Provisional application No. 61/419,508, filed on Dec. 3, 2010, provisional application No. 61/462,097, filed on Jan. 28, 2011.

(51) Int. Cl.
*A61M 5/00* (2006.01)

(52) U.S. Cl.
USPC .......................................................... 604/111

(58) Field of Classification Search
USPC .......................................................... 604/111
See application file for complete search history.

(56) References Cited

U.S. PATENT DOCUMENTS

| | | |
|---|---|---|
| 3,245,567 A | 4/1966 | Knight |
| 3,747,751 A | 7/1973 | Miller et al. |
| 4,216,872 A | 8/1980 | Bean |
| 4,313,539 A | 2/1982 | Raines |
| 4,420,085 A | 12/1983 | Wilson et al. |
| 4,571,242 A | 2/1986 | Klein et al. |
| 4,667,837 A | 5/1987 | Vitello et al. |
| 4,726,483 A | 2/1988 | Drozd |
| 4,832,695 A | 5/1989 | Rosenberg et al. |
| 4,844,906 A | 7/1989 | Hermelin et al. |
| 5,009,323 A | 4/1991 | Montgomery et al. |
| 5,135,496 A | 8/1992 | Vetter et al. |
| 5,165,560 A | 11/1992 | Ennis, III et al. |
| 5,328,474 A | 7/1994 | Raines |
| 5,458,580 A | 10/1995 | Hajishoreh |
| 5,558,648 A | 9/1996 | Shields |
| 5,624,402 A | 4/1997 | Imbert |
| 5,785,691 A | 7/1998 | Vetter et al. |
| 5,807,343 A | 9/1998 | Tucker et al. |
| 5,883,806 A | 3/1999 | Meador et al. |
| 6,000,548 A | 12/1999 | Tsals |
| 6,027,482 A | 2/2000 | Imbert |
| 6,068,614 A | 5/2000 | Kimber et al. |
| 6,126,640 A | 10/2000 | Tucker et al. |
| 6,190,364 B1 | 2/2001 | Imbert |
| 6,193,688 B1 | 2/2001 | Balestracci et al. |
| 6,196,998 B1 | 3/2001 | Jansen et al. |
| 6,280,418 B1 | 8/2001 | Reinhard et al. |
| 6,394,983 B1 | 5/2002 | Mayoral et al. |
| 6,485,460 B2 | 11/2002 | Eakins et al. |
| 6,520,935 B1 | 2/2003 | Jansen et al. |
| 6,565,529 B1 | 5/2003 | Kimber et al. |
| 6,581,792 B1 | 6/2003 | Limanjaya |

(Continued)

*Primary Examiner* — Jason Flick
(74) *Attorney, Agent, or Firm* — Malloy & Malloy, P.L.

(57) ABSTRACT

A closure assembly structured for use with a female luer connector operative to indicate an attempted tampering or access thereto. A flow restrictor is movably and removably disposed within a housing and includes a male connector, such as a male luer connector, inserted in flow restricting engagement within an interior port of the female luer connector. An indicator member is removably connected within the housing and a drive assembly associated with both the flow restrictor and the housing is operable to dispose the male connector in flow restricting engagement within the female connector. Attempted removal of the closure assembly from the female connector will detach an indicator member from the housing and visually expose it, thereby indicating attempted access.

18 Claims, 9 Drawing Sheets

(56) References Cited

U.S. PATENT DOCUMENTS

| | | |
|---|---|---|
| 6,585,691 B1 | 7/2003 | Vitello |
| 6,726,652 B2 | 4/2004 | Eakins et al. |
| 6,821,268 B2 | 11/2004 | Balestracci |
| 6,921,383 B2 * | 7/2005 | Vitello .......... 604/111 |
| 6,942,643 B2 | 9/2005 | Eakins et al. |
| 7,141,286 B1 | 11/2006 | Kessler et al. |
| 7,374,555 B2 | 5/2008 | Heinz et al. |
| 7,425,208 B1 | 9/2008 | Vitello |
| 7,588,563 B2 | 9/2009 | Guala |
| 7,632,244 B2 | 12/2009 | Buehler et al. |
| 7,641,636 B2 | 1/2010 | Moesli et al. |
| 7,735,664 B1 | 6/2010 | Peters et al. |
| 7,762,988 B1 | 7/2010 | Vitello |
| 8,348,895 B1 | 1/2013 | Vitello |
| 8,353,869 B2 | 1/2013 | Ranalletta et al. |
| 8,616,413 B2 | 12/2013 | Koyama |
| 2002/0133119 A1 | 9/2002 | Eakins et al. |
| 2004/0064095 A1 | 4/2004 | Vitello |
| 2004/0116858 A1 | 6/2004 | Heinz et al. |
| 2004/0225258 A1 | 11/2004 | Balestracci |
| 2012/0064515 A2 | 3/2012 | Knapp et al. |

* cited by examiner

TAMPER INDICATING CLOSURE ASSEMBLY

CLAIM OF PRIORITY

The present Non-Provisional patent application claims priority pursuant to 35 U.S.C. Section 119 to a prior filed Provisional patent application, namely, that having Ser. No. 61/419,508 filed on Dec. 3, 2010, as well as to another prior filed Provisional application, namely, that having Ser. No. 61/462,097 filed on Jan. 28, 2011, the contents of both being incorporated herein by reference in their entireties.

BACKGROUND OF THE INVENTION

1. Field of the Invention

A closure assembly for use on a female luer connector or another generally similar type of connector of the type used with intravenous (IV) administration assemblies for the dispensing of IV fluid and/or the adding of medicine or other agents to the liquid dispensed from the IV container. The closure assembly is structured to establish a closed, fluid sealing connection to the female luer connector and provide an obvious indication of tampering or attempted access to the female connector or contents of the IV reservoir or container associated therewith.

2. Description of the Related Art

In the medical field, it is a relatively common procedure to administer fluids to a patient by intravenous (IV) infusion. A variety of IV assemblies are known and are useful in the treatment of a number of medical conditions, in that a variety of fluids and/or medicines can be administered to a patient utilizing such assemblies over a prescribed period of time and in controlled amounts. In use, a conventional IV administration assembly typically includes a reservoir or container, in the form of a bottle or more commonly, a flexible material bag, suspended on a pole or like support structure located substantially adjacent to the patient being treated, typically in an elevated relation thereto. In addition, the IV fluid flows from the supported and elevated IV bag to the patient by means of elongated, flexible tubing connected at a proximal end to the IV bag and at the other distal end, connected intravenously to the patient by way of a catheter or like structure. The IV delivery tube is also structured to connect at one end to or be interconnected with an appropriate connector, often having somewhat of a "Y" shape, that is associated with the IV assembly and in fluid communication with either the contents of the IV bag or alternatively, with the catheter in use on the patient for intravenous administration of fluids and medicines.

One such connector may be in the form of a female connector attached to the IV bag or other container and disposed in fluid communication with the contents thereof. An appropriate female connector may be in the form of a female luer connector which at least partially defines, along with a male luer connector, a "luer lock" connector assembly, as is well known in the medical profession. The male luer connector is secured to the IV delivery tubing, such as at the proximal end, and is specifically structured to be attached to the female luer connector in a manner which establishes fluid communication with contents of the IV container, and facilitates a flow of the IV fluid from the IV container through the connected male and female luer connectors. As a result, fluid flow between the patient and the interior of the IV bag is established. As is also well known, various types of valves and/or flow regulating devices may be operatively associated with the IV assembly to regulate the amount of fluid or rate of fluid delivery to the patient during the administration procedure.

In addition, known IV containers or reservoirs may incorporate an additional female luer connector or other female type connector which are disposed in fluid communication with the IV delivery tubing, such as but not limited to at the IV bag. This additional female luer connector is provided to administer additional liquid agents, such as pain medication, antibiotics, and/or other medicinal compositions, to the IV fluid being delivered to the patient. However, such an additional female luer connector may remain unused or may be accessed at a time subsequent to the initiation of the IV fluid administration, such as when additional medication or another composition is required or prescribed.

In periods of non-use, it is important to maintain a female luer connector in a closed and fluid sealed condition in order to maintain sterility, and also, the integrity of the IV fluid prior to use. This is also important in order to restrict unauthorized access to the IV fluid and even to the female luer connector. Therefore, there is a need in the medical field for an efficient, effective and easily applied closure assembly that would be capable of closing and sealing a female connector during periods of its non-use. If any such closure assembly were developed, it should also be structured to provide a clear visual indication whenever there has been tampering or other attempted access to the female luer connector and/or contents of the IV container. Moreover, if any such closure assembly were developed, it should also be structured for efficient attachment to the female luer connector and so as to prevent re-attachment to the female connector, once unauthorized access has been attempted or accomplished. If any such closure assembly were developed, it should also be capable of being removed from the female connector in a manner which provides the aforementioned visual or other appropriate indication of complete, partial or other attempted access to the female luer connector.

Finally, the structural components as well as the operational characteristics of any such closure assembly developed should ideally also provide a sufficient degree of reliability relating to the secure closing and sealing of the female connector of the IV container, while clearly indicating when access thereto has occurred.

SUMMARY OF THE INVENTION

The present invention is intended to present a solution to these needs which remain and in this field of art and as such, is directed to a closure assembly that is specifically, but not exclusively, structured for the closing and sealing of a female connector such as, but not limited to, a female luer connector having an interior flow port. Such female connectors are commonly used, along with a cooperatively structured male luer connector, as part of a "luer lock" connector assembly found on and/or used in combination with a variety of medical devices, including intravenous (IV) dispensing or administration assemblies. As such, the female luer connector or another generally similar type of connector is disposed and structured to facilitate the dispensing of the IV fluid from the IV container and/or the addition of medicine or other agents to the IV liquid prior to or concurrent with its administration to a patient. Moreover, the female luer connector, as described above, facilitates the addition of medicine or other composition by means of a pre-loaded syringe which can be absent the use of a needle. Specifically, and as has become relatively commonplace following awareness of the AIDS virus and how AIDS is transmitted, needle-less syringes may be pre-loaded with a medicine or substance to be given to a patient. These needle-less syringes typically include an elongated, male-type of discharge nozzle that is dimensioned and configured to be received within the access port of a female luer connector and thereby, eliminate the need for an actual needle to be attached to the syringe.

Accordingly, and in order to restrict or at least provide a clear indication of attempted access to the female connector and the contents of the IV container, the present invention is directed to a closure assembly, which is connected in fluid sealing relation to the female connector. The structure of the closure assembly restricts its removal from the female luer connector without providing an obvious indication that tampering or attempted access has occurred. Also, once removed from the female connector, the tamper evident closure assembly of the present invention is ideally structured so that it cannot be re-attached, in an attempt to hide an unauthorized attempted at access.

Turning now to the structural and operative features of the present inventive closure assembly, they include a housing that has an at least partially hollow interior and of a sufficient capacity to enclose and at least partially retain a flow restrictor therein. In addition, the housing includes a closed end portion and an oppositely disposed open end. The open end is of sufficient dimension to at least partially receive a portion of the female connector there-through into interactive connection with the flow restrictor. The flow restrictor is movably and removably disposed within the housing and is structured to be threaded or otherwise appropriately connected to the female connector concurrently to the closure assembly being attached to the female connector.

In addition, an indicator member is fixedly but preferably removably connected to the housing and is disposed on the interior thereof in at least partially surrounding relation to a corresponding part of the flow restrictor. At least one, but possibly a plurality of frangible members serve(s) to detachably interconnect the indicator member to the interior surface of the housing. The indicator member is thereby initially fixed, but detachable from the housing. Moreover, when fixed to the housing the indicator member and the aforementioned closed end portion of the housing are cooperatively disposed to movably retain the flow restrictor within the housing in a position which facilitates the movement of the flow restrictor into a connected orientation with the female luer connector.

As set forth above, the various preferred embodiments of the closure assembly of the present invention are specifically, but not exclusively, structured to close and seal a female luer connector of the type which may be associated with an IV dispensing assembly. Therefore, structural components associated with the flow restrictor further include a male plug which, in accordance with one aspect of the present invention, may include a structure which is equivalent or substantially similar to a male luer connector. As such, the male plug is dimensioned and configured to be inserted in flow restricting engagement within the interior access port of the female connector so as to prevent fluid flow therethrough and/or access to the contents of the IV container or other medical device associated with the female connector.

Additional structural and operative details of the present inventive closure assembly facilitate its attachment to a female connector in flow restricting engagement therewith. Further, once the closure assembly is attached to the female connector it cannot be removed there-from without providing a clear indication of tampering and/or attempted access to the female connector and the contents of the IV container. Also, once removed from the female connector, the closure assembly cannot be re-attached thereto in an operative manner.

The closure assembly of the present invention preferably also includes a drive assembly. In the illustrated embodiment described in detail hereinafter, the drive assembly can comprise a first and a second drive segment, wherein the first drive segment is connected to or mounted on the closed end portion of the housing. The second drive segment is cooperatively disposed relative to the first drive segment by being connected to or mounted on a portion of the flow restrictor which is disposed in confronting engagement with the interior surface of the closed end portion. In at least one preferred embodiment of the present invention, the first and second drive segments each include what may be referred to as a rotational type "ramp and cliff" drive structure. In addition, the ramp and cliff drive structures of each of the first and second drive segments may be mirror images of one another and substantially reversely oriented. As a result, interaction between the confronting surfaces of the first and second drive segments during rotation of the housing and the connected closed end portion, in a single predetermined direction, will cause rotation and axial movement of the flow restrictor and male plug attached thereto. As a result, the plug will be forced into the aforementioned inserted and flow restricting engagement within the interior port of the female connector. Therefore, the drive assembly of the present invention may be described as a "one way drive assembly" due to the ability to rotate and axially position the flow restrictor and male plug into flow restricting engagement with the interior port of the female connector, only upon rotation of the housing in a single direction.

More specifically, the rotational type ramp and cliff structures formed on each of the first and second drive segments provide concurrent rotation of the housing and the flow restrictor, when the housing is rotated in only one, predetermined direction. Rotation of the housing in a direction opposite from the one, predetermined direction will result in the ramp and cliff drive structures being disposed out of driving relation to one another and a "slippage" or relative sliding movement there between. Therefore, it should be apparent that the flow restrictor and male plug fixedly secured thereto are movably and rotationally mounted within the interior of the housing. Due to the cooperative structuring of the first and second drive segments, the male plug will be inserted in flow restricting relation within the interior access port of the female connector as the housing is rotated in the one predetermined direction. However, rotation of the housing in the opposite direction will not accomplish a removal of the flow restrictor from its connection with the female connector or the male plug from the inserted, flow restricting relation with the interior access port of the female connector and therefore will not serve to remove the housing of the closure assembly from the female connector.

Removal of the housing from the female connector, in order to access the flow restrictor and eventually the contents of the IV container, can be effectively accomplished by exerting an axially directed "pull force" on the housing. Such an axially directed force, in order to be sufficient to remove the housing from the female connector must be adequate to detach the indicator member from the interior of the housing. Such detachment will be a result of the axial force exerted on the housing being sufficient to break or rupture the one or more frangible members which connect the indicator member to the interior of the housing, as set forth above. When the housing is detached, the indicator member, preferably in the form of a color-coded ring or like structure, will remain and be readily observable in surrounding relation to the now exposed flow restrictor, which will remain connected to the female connector. Therefore, a clear indication of tampering or attempted access to the contents of the IV container and/or female connector will be effectively provided by the observance of the exposed indicator member.

Accordingly, the one or more preferred embodiments of the closure assembly of the present invention provide a sufficient and reliable structure for closing and sealing a female luer connector or other female connector of the type which may be associated with an IV container or other device. The closure assembly is further structured to provide a clear indication of tampering or attempted access to the female connector and other devices which the female connector may be associated.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT(S)

Figure 1:
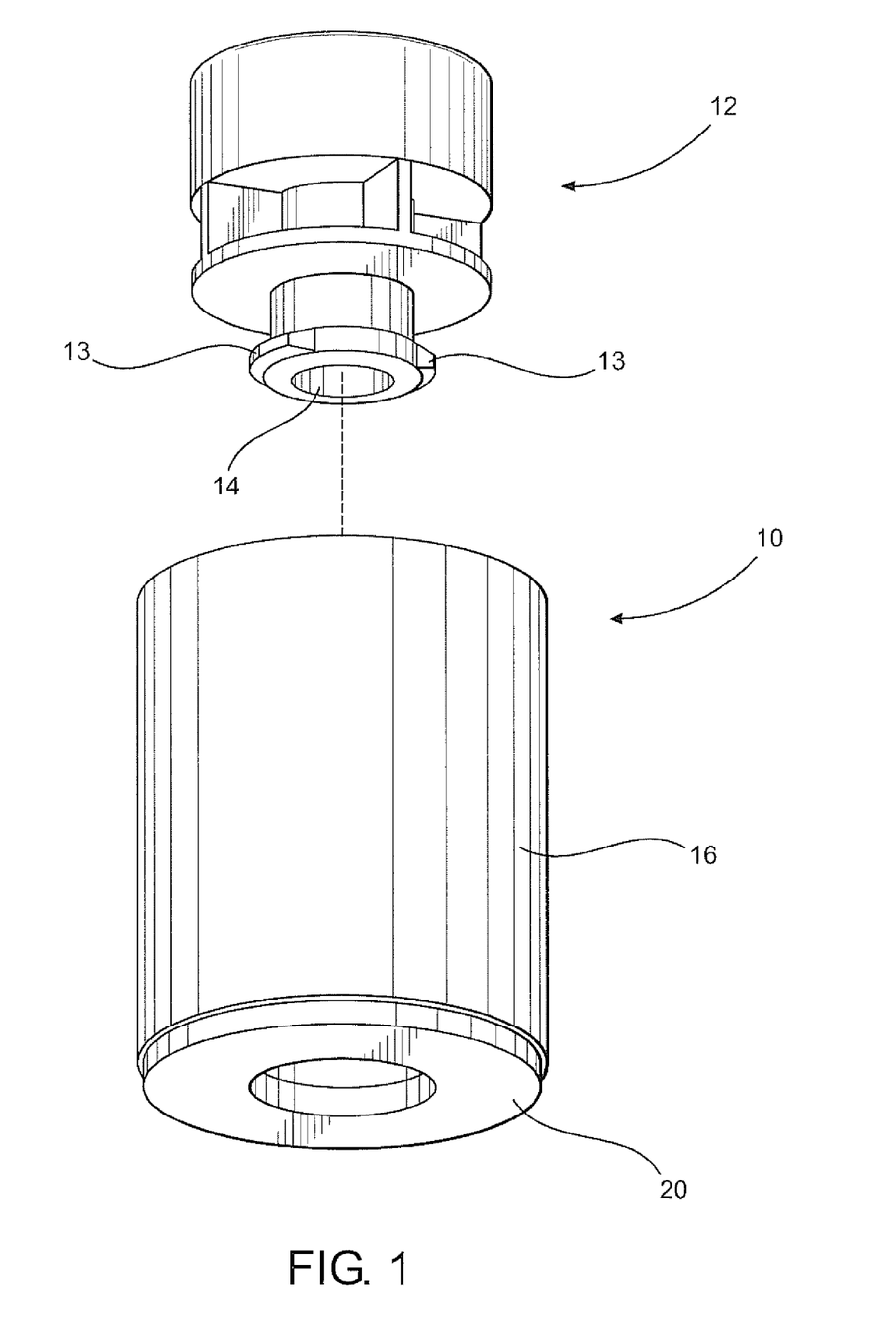
FIG. 1 is a perspective view in exploded form of the closure assembly of the present invention in a position for attachment to a female connector, such as a female luer connector, of the type used with IV dispensing assemblies.
Figure 2:
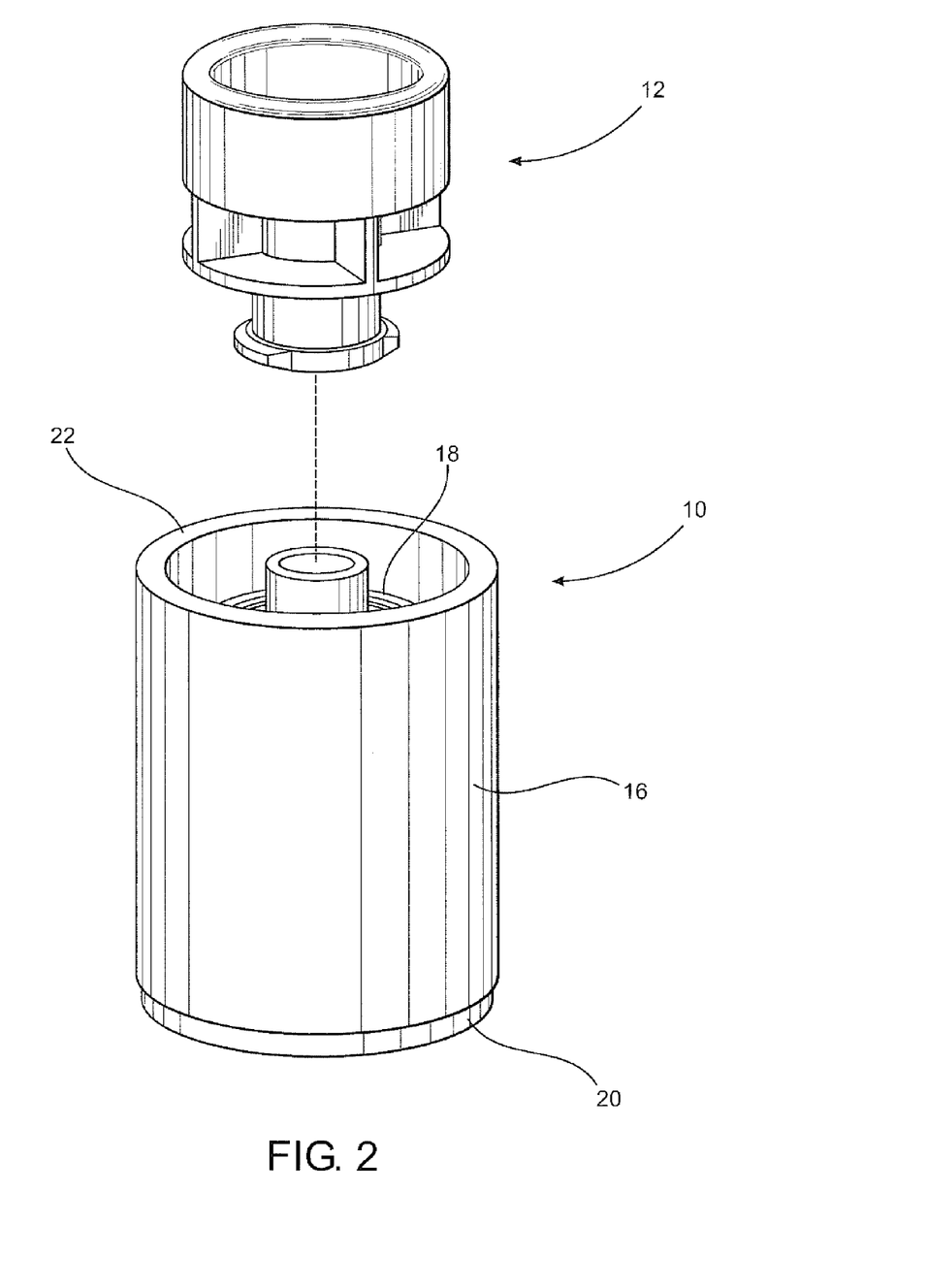
FIG. 2 is a perspective view in exploded form of the embodiment of FIG. 1 disclosing interior portions of the closure assembly.

As represented in the accompanying drawings, the present invention is directed to a closure assembly generally indicated as 10 structured to close and provide a fluid seal with a female connector generally indicated as 12, as is perhaps best shown in FIGS. 1 and 2. In at least one preferred embodiment, the female connector 12 is more specifically defined and structured as a female luer connector including, as shown in FIG. 1, an interior port or access port 14 structured for the passage of fluid therethrough from a IV container or IV bag, or other reservoir with which the female luer connector 12 is associated. By way of example, a female luer connector or other female type connector may be connected to and/or directly associated with an intravenous (IV) dispensing assembly (not shown) of the type commonly used to administer fluid to a patient over a prescribed period of time, as has been described previously herein. As such, elongated flexible tubing having a male luer connector secured to one end may be attached to the female connector 12, shown in FIG. 2, by insertion within the access port 14 in order to dispense the fluid contents from the IV container to the patient. In addition, the female luer connector 12 may also be utilized to add an additional agent or composition to the fluid being dispensed from the IV container. In such situations, a preloaded syringe having an elongated nozzle may be inserted into the access port 14 of the female connector 12.

Accordingly, it is desirable to maintain the female connector 12 closed and sealed when not being used in order to prevent inadvertent and/or unauthorized access to the contents of the IV container with which the female connector 12 is associated. Therefore, at least one embodiment of the closure assembly 10 includes structural and operative features which accomplish a closed, fluid sealing of the female connector 12. Further, the closure assembly 10 is ideally structured to provide a clear indication of tampering or attempted access to the female connector 12 and the contents of the IV container with which it is associated.

As represented in FIGS. 1-6, the closure assembly 10 includes a housing 16 having an at least partially hollow interior 18 of sufficient dimension and configuration to hold additional structural components operatively associated with the closure assembly 10. Also, the housing 16 includes a closed end portion 20 and an oppositely disposed open end 22. The open end 22 is sufficiently dimensioned and configured to allow at least a portion of the female luer connector 12 to pass therethough. Therefore, when the closure assembly 10 is operatively connected to the female connector 12, at least a portion of the female connector 12 associated with the interior female port 14 is disposed at least partially within the interior 18 of the housing 16 by passing through the open end 22.

Figure 3:
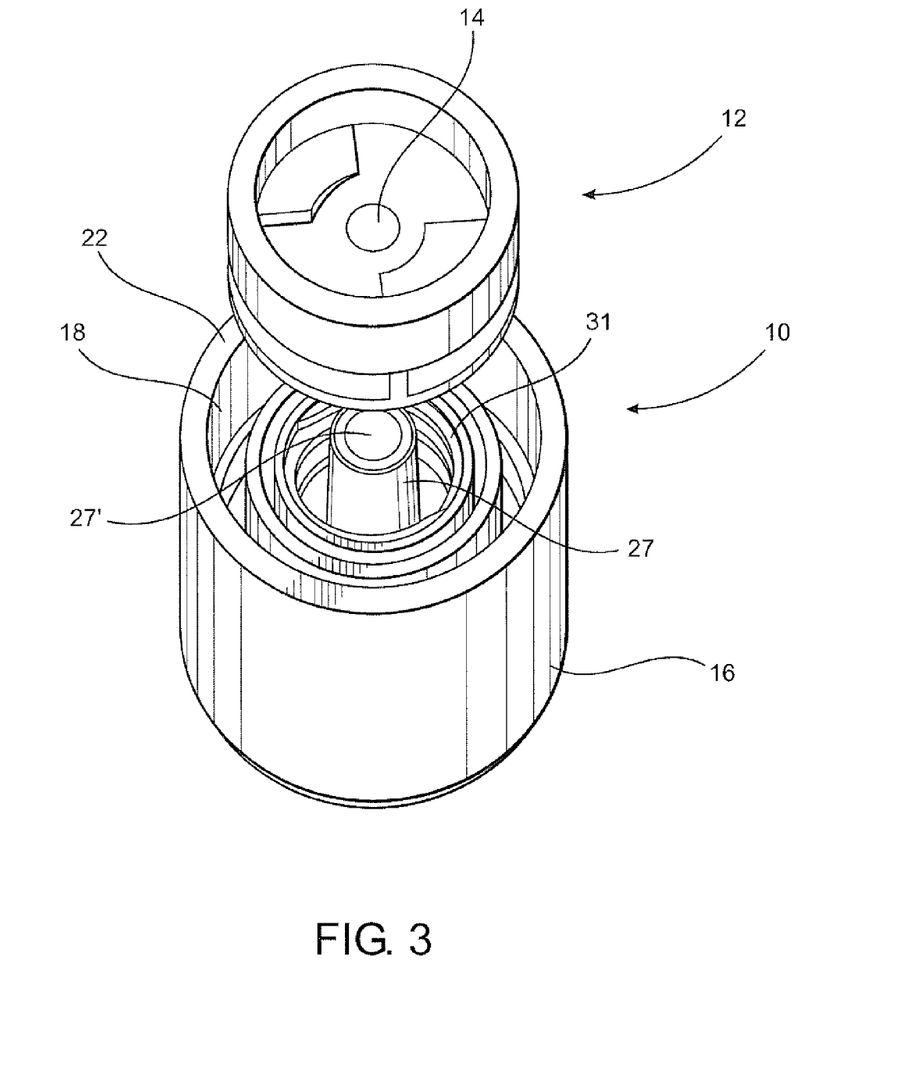
FIG. 3 is a top perspective view of the embodiments of FIGS. 1 and 2 disclosing further structural features on the interior of the closure assembly of the present invention.
Figure 4:
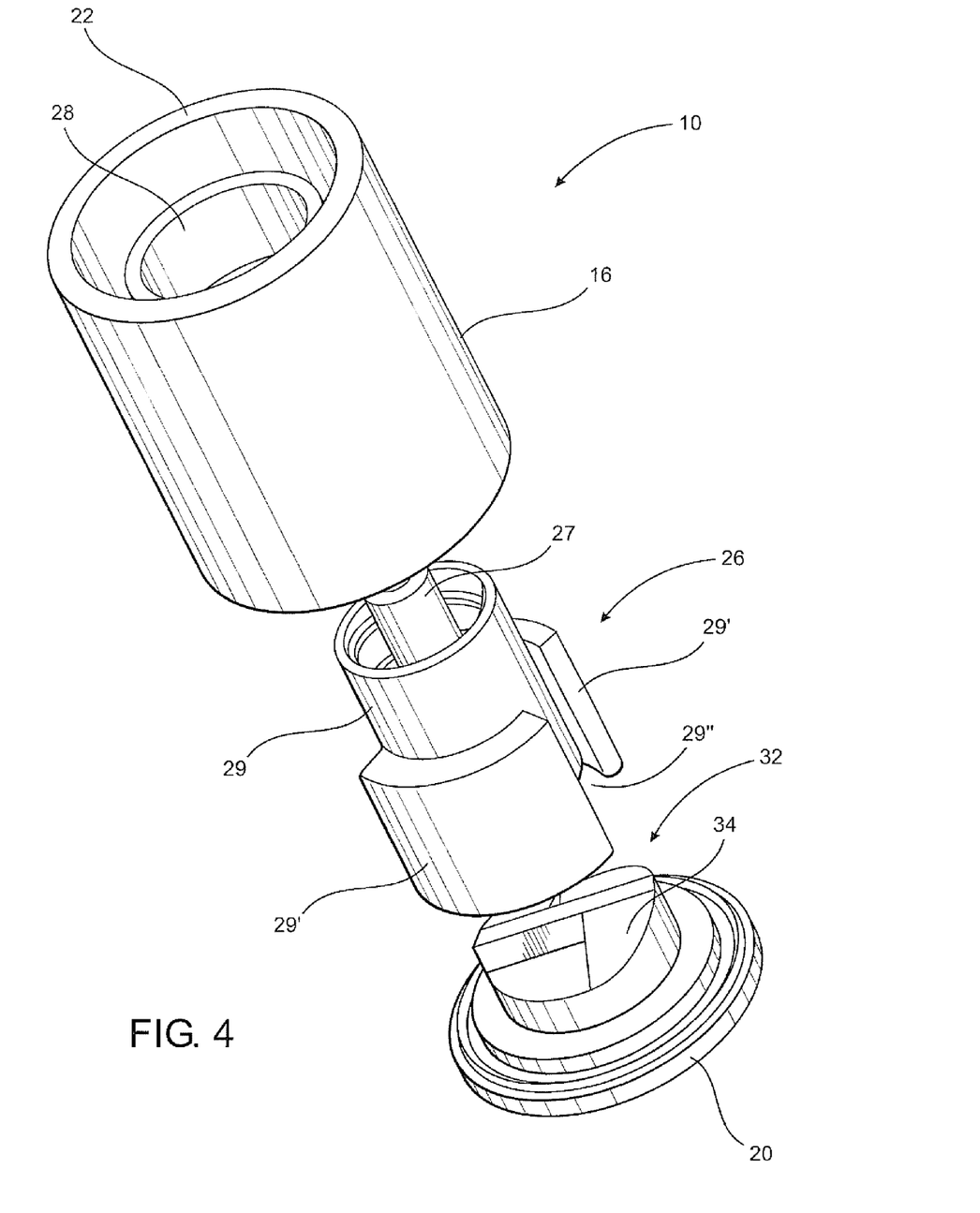
FIG. 4 is a perspective view in exploded form of the operative and structural components of at least one preferred embodiment of the closure assembly of the present invention.
Figure 5:
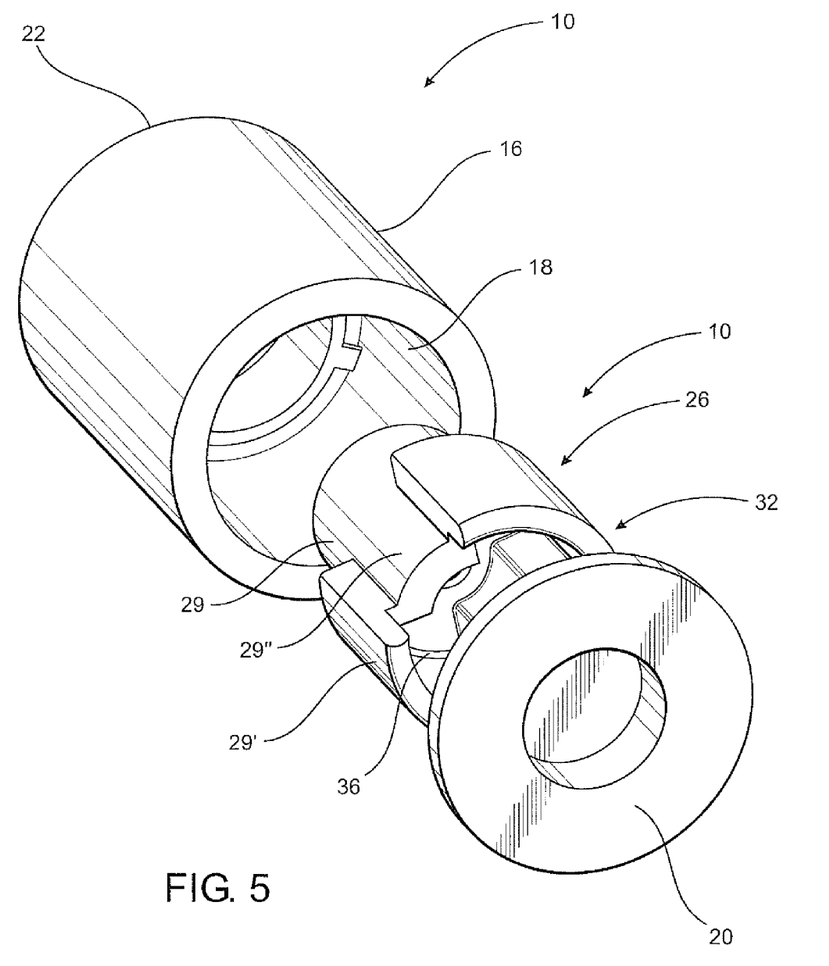
FIG. 5 is a perspective view of the embodiment of FIG. 4 showing additional interior structural features of the closure assembly of the present invention.
Figure 6:
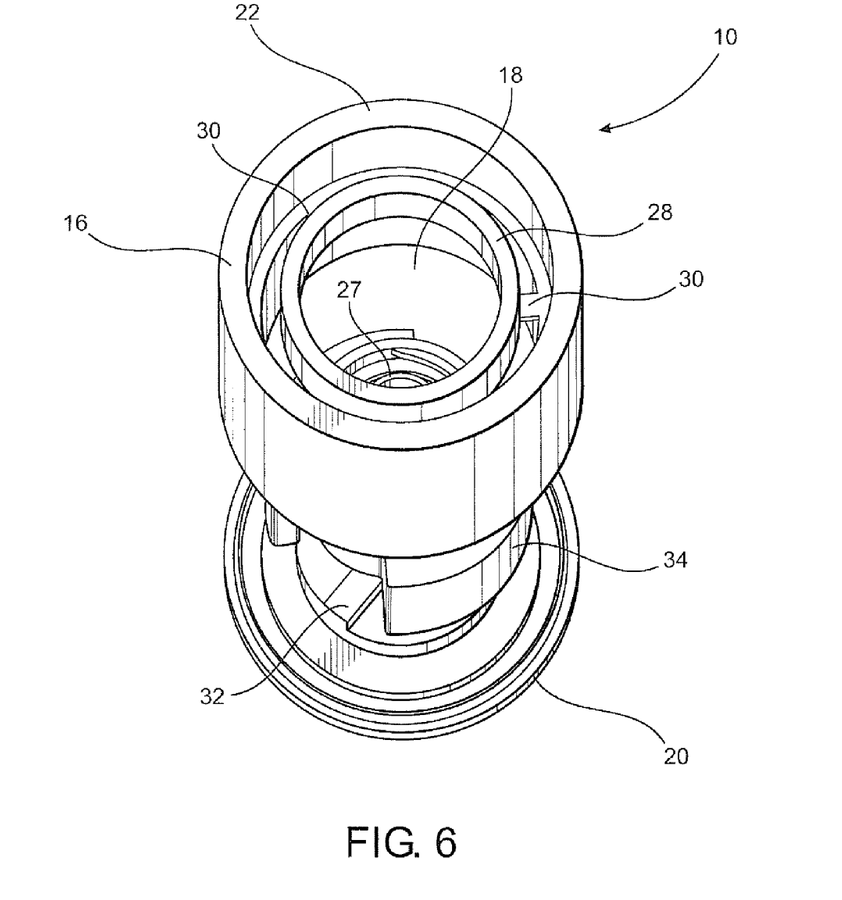
FIG. 6 is a top perspective view in exploded form representing additional structural features of the closure assembly of the embodiments of FIGS. 4 and 5.

FIGS. 1-3 collectively and schematically represent relative orientations of the closure assembly 10, including housing 16, and the female luer connector 12 immediately prior to interconnection therebetween. In contrast, FIGS. 4-6 provide schematic representations of the different structural components of the closure assembly 10 and the operative features associated therewith. Moreover, at least one embodiment of the closure assembly 10 is represented in an unassembled state for purposes of clarity. It is emphasized that the closure assembly 10 will be fully assembled as disclosed in FIGS. 1-3 prior to connection to the female luer connector 12.

With primary reference to FIGS. 4-6, the housing 16 includes the closed end portion 20 being fixedly connected to one end thereof, which is oppositely disposed to the open end 22. As set forth above, the at least partially hollow interior 18 of the housing 16 is dimensioned and configured to receive a flow restrictor generally indicated as 26 therein. Further, an indicator member 28 preferably includes an annular configuration having an interior dimension sufficient to receive at least a portion of the flow restrictor 26 therethrough, as also represented in FIGS. 2 and 3. The indicator member 28 is fixedly but detachably secured to the interior surface of the housing 16 by at least one but possibly a plurality of frangible members 30. One or more frangible members 30 are fixedly but detachably secured in interconnecting relation between the interior surface of the housing 16 and the exterior surface of the indicator member 28. Moreover, the one or more frangible members 30 are specifically structured to break or rupture and thereby be detached from their initially interconnecting relation between the housing 16 and indicator member 28 upon a sufficient force including, but not limited to, an axial force, being applied to the housing 16, as set forth in greater detail hereinafter.

Therefore, the indicator member 28 is initially disposed in fixed interconnection on the interior of the housing 16. In contrast, the flow restrictor 26 is movably disposed within and removable from the interior 18 of the housing 16. As clearly represented in the accompanying Figures, the flow restrictor 26 is at least initially movably and removably disposed and retained between the fixedly connected closed end portion 20 and the initially fixed indicator member 28. As a result, the flow restrictor 26 is disposed and dimensioned to move rotationally and axially within the interior 18 between the closed end portion 20 and the indicator member 28. Such movement of the flow restrictor 26 can be accomplished, at least initially, before connection of the closure assembly 10 to the female luer connector 12. As will be more fully explained, the rotational and axial movement of the flow restrictor 26 serves to accomplish the connection of the closure assembly 10 to the female connector 12 and the positioning of the flow restrictor 26 into a closed, fluid sealing relation within the interior access port 14 of the female connector 12 by operation of a drive assembly, generally indicated as 32.

With primary reference to FIGS. 3-6, the intended closed, fluid sealing connection of the closure assembly 10 with the female connector 12 is facilitated by the structuring of the flow restrictor 26 to include a male plug 27. Moreover, in at least one preferred embodiment, the male plug 27 is structured to substantially define a male luer connector. More specifically, in at least one embodiment the flow restrictor 26 includes the male plug 27 having an exterior, tapered or frusto-conical configuration and a closed outer end portion 27'. The male plug 27 is integrally or otherwise fixed to the remainder of the flow restrictor 26 and is disposed to be inserted in flow restricting engagement within the interior access port 14 of the female connector 12.

Yet additional features of the flow restrictor 26 include a casing 29 disposed in surrounding, outwardly spaced relation to the male plug 27. Relative dimensions and positions of the casing 29 and the male plug 27 facilitate the insertion and fluid restricting engagement of the male plug 27 into the interior of the port 14 of the female restrictor 12 when the closure assembly 10 is connected to the female connector 12 in the intended manner.

Figure 5A:
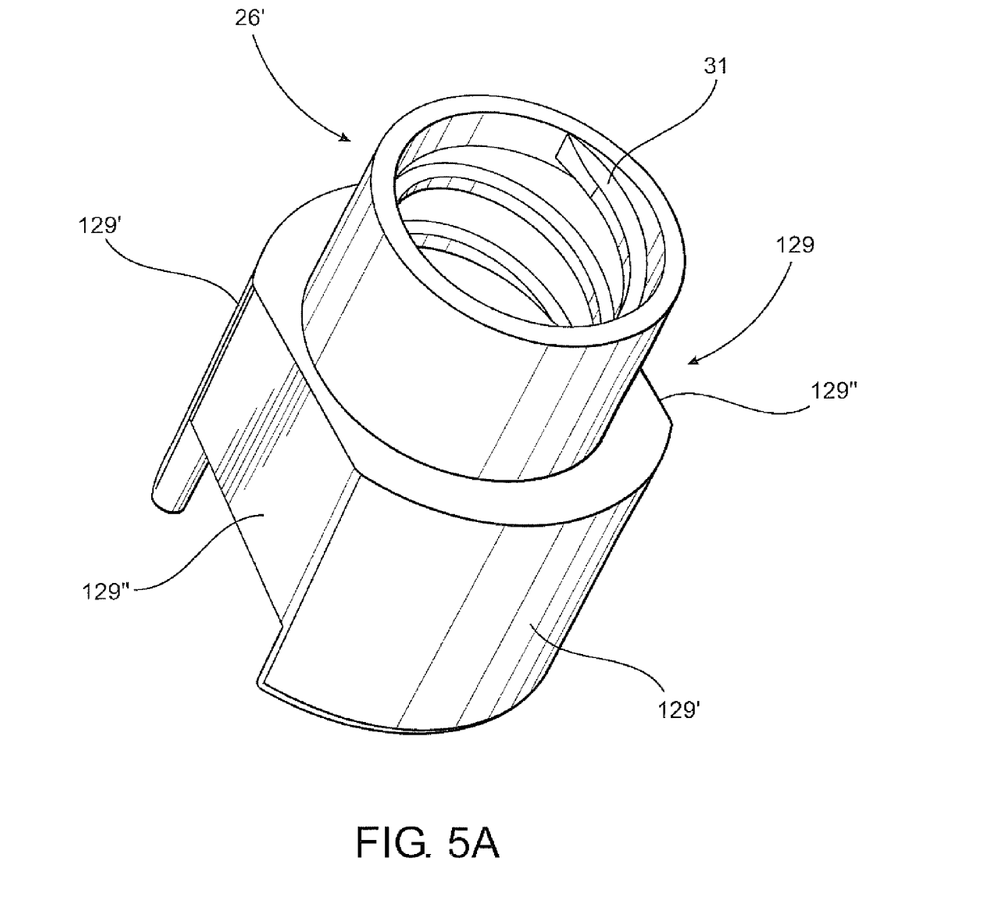
FIG. 5A is a perspective view of another preferred embodiment of a component of the closure assembly of the present invention.

As represented in FIGS. 4-5, the casing 29 also includes an exterior structure which may include curved segmented portions 29' separated by spaces 29" which are disposed on opposite sides of the casing 29. The dimension and disposition of the segmented portions 29' may facilitate a movable but secure positioning of the flow restrictor 26 on the interior 18 of the housing 16. Also, the configuration of the exterior of the casing 29, as collectively defined by the alternating curved segments 29' and spaces 29" may facilitate the gripping and manual rotation of the flow restrictor 26 relative to the female connector 12 by an individual, when such is required. However, in the additional embodiment of FIG. 5-A, the flow restrictor 26' is structurally modified and generally indicated as 129. As shown, the exterior of the casing 129 includes an exterior structure that offers a smoother configuration with less sharp edges, so that manipulation, when needed, is facilitated, and thus, the casing 129 comprises oppositely disposed curved segments 129' separated from one another by oppositely disposed substantially flat segments 129". Therefore, in the embodiment of FIG. 5-A, the spaces 29" have been eliminated and replaced by the flat segments 129". As a result, the configuration of the exterior of the casing 129, as collectively defined by the alternating curved segments 129' and flat segments 129" may further facilitate the gripping and manual rotation of the flow restrictor 26' relative to the female connector 12 by an individual, when such is required.

The flow restrictor 26 is also cooperatively structured with the female connector 12 to accomplish a stable connection therewith. More specifically, attachment of the flow restrictor 26 in the inserted, flow restricting relation to the interior access port 14 of the female connector 12 is preferably accomplished by a threaded interconnection. Such cooperative structuring comprises the female luer connector 12 having outwardly extending ears or like projections 13. In cooperation therewith, a threaded portion(s) 31 of the flow restrictor 26 are disposed on an interior surface of the casing 29 of the flow restrictor 26. The interior threaded portion or surface 31 is disposed and structured to receive the protruding connecting ears 13 when the flow restrictor 26 and housing 16 are rotated relative to the female connector 12, as set forth above. As also indicated above, the rotation of the housing 16 in the predetermined one direction will cause the rotational movement of the flow restrictor 26 through interaction of the two drive segments 34 and 36 of the drive assembly 32. Such rotation of the flow restrictor 26 will cause a threaded engagement of the connecting ears 13 of the female connector 12 and the internally threaded surface or portion 31 of the flow restrictor 26 and a resulting axial movement between the flow restrictor 26 and the female connector 12. Moreover, threaded interaction of the ears 13 and the threaded portion 31 during concurrent rotation of the housing 16 and the flow restrictor 26 will facilitate the axial placement of the male plug 27 into an inserted, fluid sealing relation within the interior port 14 of the female connector 12.

As set forth above, attachment of the closure assembly 10 in a closed, fluid sealing engagement with the female connector 12 is facilitated by the operative and structural features of the drive assembly 32. As utilized, the drive assembly 32 may be more specifically described as a one way drive assembly and includes the first drive segment 34 integrally or otherwise fixedly connected to an interior portion the closed end portion 20. The drive assembly 32 also includes a second drive segment 36 integrally or otherwise fixedly secured to an end or other appropriate portion of the flow restrictor 26 so as to be disposed in engaging, interactive relation to the first drive segment 34. Each of the first and second drive segments 34 and 36 are cooperatively structured to define the aforementioned one way drive assembly by including the aforementioned "ramp and cliff" drive structure. More specifically, the ramp and cliff drive structures of each of the first and second drive segments 34 and 36 may comprise mirror image patterns, in relief of one another, as they are mounted on corresponding, confronting surfaces of the closed end portion 20 and flow restrictor 26, respectively. As described, the closed end portion 20 is fixedly secured to the remainder of the housing 16 and rotates therewith, while the flow restrictor 26 is movable within the housing 16. When assembled, the first drive segment 34, movable with the closed end portion 20, is disposed in confronting relation with the second drive segment 36, which is movable with the flow restrictor 26.

Therefore, a rotation of the housing 16 in a predetermined, single direction will cause a driving engagement of the first drive segment 34 with the second drive segment 36 and a forced, concurrent rotation of the flow restrictor 26 and male plug 27, with the housing 16. Continued rotation of the housing 16 and the flow restrictor 26 in the same, predetermined direction will result in a rotational and axial movement of the male plug 27 into an inserted, fluid flow restricting engagement within the interior port 14 of the female connector 12 as well as a threaded or other stable type connection of the flow restrictor 26 to the female connector 12. However, due to the structuring and relative orientations of the ramp and cliff structures of both the first and second drive segments 34 and 36, rotation of the housing 16 in a direction opposite to the one, predetermined preferred direction, will result in a slippage or sliding of the first and second drive segments 34 and 36 relative to one another. Therefore, rotation of the housing in this opposite direction will not accomplish removal of the male plug 27 from the inserted, fluid flow restricting engagement within the interior port 14 of the female connector 12 or removal of the housing 16 from the female connector 12.

As a result of the above, access to the interior access port 14 of the female connector 12 and accordingly the contents of a reservoir with which the female connector 12 may be associated is primarily, if not exclusively, accomplished by a pulling, substantially axially directed, force being applied to the housing 16. The degree of axial force applied to the housing 16, which allows it to be removed from the female connector 12 will be sufficient to cause a rupturing or breakage of the one or more frangible members 30. In turn, the indicator member 28 will be detached from the interior of the housing 16 and remain in surrounding relation to the exterior of the flow restrictor 26 which will still be threaded or otherwise connected to the female connector. Detachment of the housing 16 from the female connector 12 and the indicator member 28 will expose both the indicator member 28 and the still connected flow restrictor 26 resulting in a clear indication of tampering or attempted access to the female connector 12 and contents of the fluid reservoir with which it is associated. Further visual enhancement of attempted tampering may be accomplished by a color coding of the indicated member 28 thereby providing a clear visual indication with minimal observation that tampering or attempted access to the female luer connector 12 has occurred.

Figure 7:
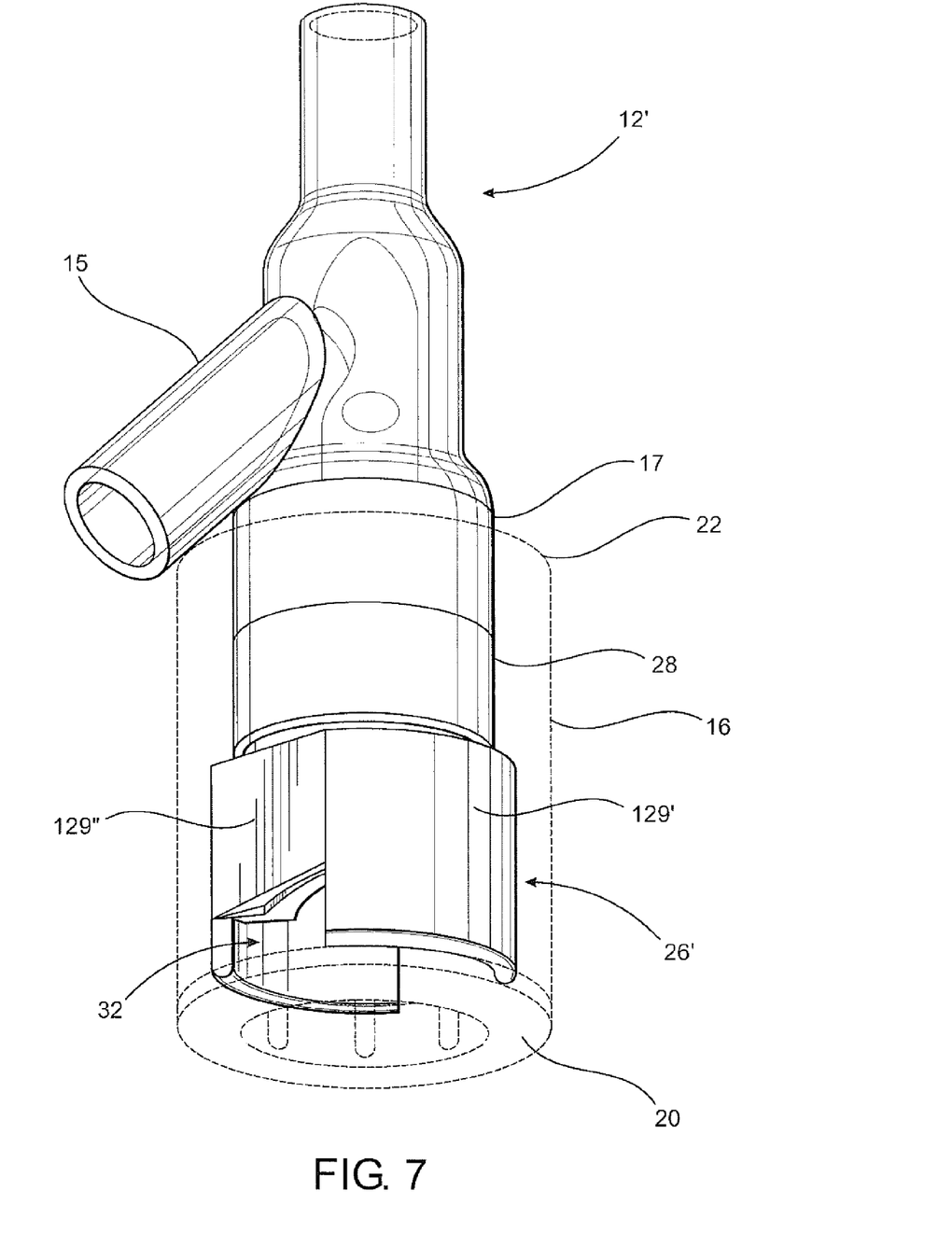
FIG. 7 is a perspective view in partial phantom of the closure assembly of the present invention connected in an operative position relative to a female connector.
Figure 8:
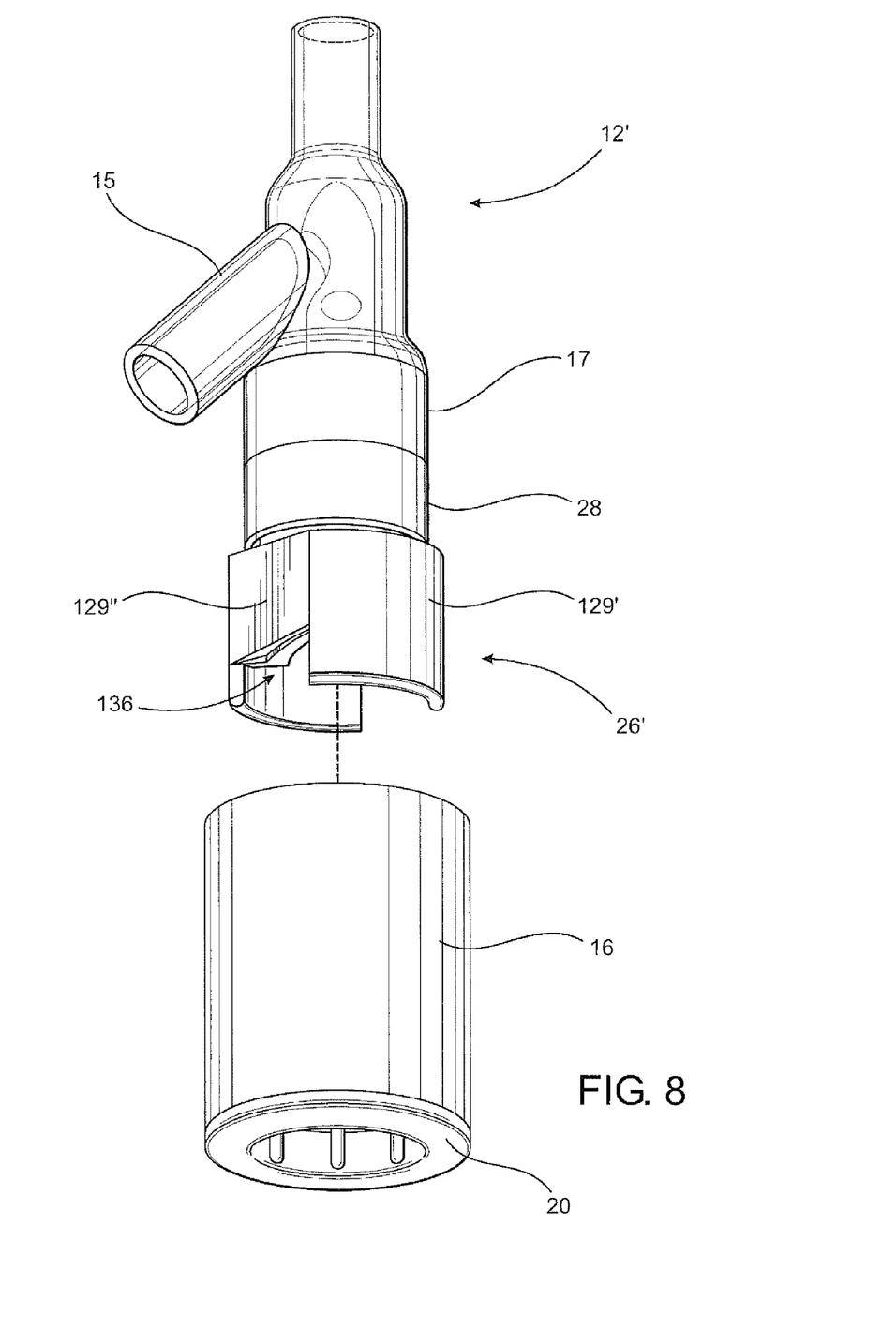
FIG. 8 is a perspective view in exploded form of the closure assembly of the embodiment of FIG. 7, wherein access to the female connector is attempted, resulting in a housing of the closure assembly having been removed exposing an indicator member evidencing the attempted access.

The structural advantages and operational versatility of the closure assembly 10 are more completely demonstrated in FIGS. 7 and 8. More specifically, FIG. 6 represents the closure assembly 10 connected to a generally "Y" shaped female connector 12' of the type that may be associated with an IV container, IV bag or other medical equipment and which incorporates the use of a female connector specifically, but not exclusively, including a female luer connector. It should be further noted that the female connector 12' may more accurately represent a connector of the type which is in use and/or commercially available as versus the schematic representation of the female connector 12 as disclosed in FIGS. 1 and 2. As such, the female connector 12' may also include a supplementary access post 15 and an exterior cover 17 disposed in surrounding or enclosing relation to the access port 14, with the latter having been shown in FIG. 1.

Accordingly, once the closure assembly 10 is in the connected position of FIG. 7, the flow restrictor 26' will serve to close and/or seal the access port 14 of the female connector 12, due to the access port 14 interacting with the male plug 27 and thereby, being closed. Also, as set forth above, when in the operative, protective position of FIG. 7, the indicator member 28 will still be attached in a non-observable position within the interior 18 of the housing or sleeve 16. In contrast, and with primary reference to FIG. 8, when authorized or unauthorized access to the female connector is 12' is attempted, a directional force will be exerted on the housing 16 resulting in its removal from its normal, covering relation to the flow restrictor 26'. As set forth above, the indicator 28 will also be detached from the housing 116, due to the applied directional force on the housing, and will become visually exposed by virtue of it remaining attached in surrounding relation the female connector 12' and immediately adjacent the flow restrictor 26. As a result, the closure assembly 10 of the present invention will provide a clear indication of tampering or attempted access to the female connector 12'.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A closure assembly for a female connector structured to indicate attempted access to the female connector, said closure assembly comprising:
   a housing including an at least partially hollow interior and a closed end portion,
   a flow restrictor movably disposed within said housing and structured for connection to the female connector,
   said flow restrictor including a male plug member dimensioned and configured for insertion in flow restricting engagement within an interior port of the female connector,
   said flow restrictor further including a casing having an interior surface disposed in surrounding, spaced relation to said plug member;
   said interior surface of said casing cooperatively structured with an exterior of the female connector to establish a connection therebetween,
   said male plug member disposed within and extending outwardly from said casing in a centrally disposed coaxial relation to said interior surface, and
   said flow restrictor and housing cooperatively structured for concurrent rotational and axial movement of said male plug member into said inserted, flow restricting engagement with the female connector.

2. A closure assembly as recited in claim 1 further comprising an indicator member fixedly and removably connected within said housing and detachable therefrom upon removal of said housing from said flow restrictor.

3. A closure assembly as recited in claim 2 wherein said indicator member comprises an annular configuration disposed in surrounding relation to at least a portion of said flow restrictor on an interior of said housing.

4. A closure assembly as recited in claim 3 further comprising at least one frangible connector disposed in removable, interconnecting relation between an interior surface of said housing and an exterior surface of said indicator member.

5. A closure assembly as recited in claim 2 wherein said indicator member is retained in surrounding relation to an exterior of said flow restrictor upon removal of said housing from said flow restrictor and connection of said flow restrictor to the female connector.

6. A closure assembly as recited in claim 1 further comprising a drive assembly disposed on both said closed end portion and said flow restrictor and cooperatively structured therewith to facilitate rotation of said flow restrictor in only one direction upon predetermined rotation of said housing relative to the female connector.

7. A closure assembly as recited in claim 1 wherein said casing includes a threaded portion disposed on said interior surface, said threaded portion disposed and configured to define a threaded engagement of said flow restrictor with an exterior of the female connector upon rotation of said male plug member relative to the female connector.

8. A closure assembly as recited in claim 1 wherein said male plug member comprises an elongated configuration having a tapered, closed exterior surface terminating in a closed outer end.

9. A closure assembly as recited in claim 8 wherein said tapered configuration and length of said male plug member is sufficient to define a fluid seal within the interior port of the female connector when disposed in said inserted, flow restricting engagement within the interior port of the female connector.

10. A closure assembly for a female luer connector structured to indicate attempted access to the female connector, said closure assembly comprising:
- a housing including an at least partially hollow interior and a closed end portion and an open end disposed in communicating relation with said hollow interior,
- an indicator member fixedly and removably connected within said housing and detachable therefrom,
- a flow restrictor movably retained within said housing between said closed end portion and said indicator member,
- said flow restrictor including a male luer connector comprising a plug, said plug disposed and structured for inserted, flow restricting engagement within an interior port of the female luer connector,
- said flow restrictor further including a casing having an interior surface disposed in surrounding, spaced relation to said plug;
- said interior surface of said casing cooperatively structured with an exterior of the female connector to establish a connection therebetween,
- said plug disposed within and extending outwardly from said casing in a centrally disposed coaxial relation to said interior surface,
- a drive assembly disposed on both said closed end portion and said flow restrictor and cooperatively structured therewith to facilitate rotation of said flow restrictor in only one direction upon a predetermined rotation of said housing relative to the female connector, and
- said housing and said flow restrictor cooperatively structured for concurrent rotational and axial movement of said plug into said inserted flow restricting engagement within the interior port of the female connector, upon said predetermined rotation of said housing.

11. A closure assembly as recited in claim 10 wherein said drive assembly comprises a first drive segment mounted on said closed end portion and a second drive segment mounted on a portion of said flow restrictor disposed in confronting relation with said closed end portion.

12. A closure assembly as recited in claim 11 wherein said first and second drive segments are cooperatively structured to rotate said flow restrictor and said plug in only one direction upon said rotation of said housing.

13. A closure assembly as recited in claim 10 wherein said casing includes a threaded portion disposed on said interior surface thereof, said threaded portion disposed and configured to define a threaded engagement of the flow restrictor with the female connector upon said concurrent rotation and axial movement of said plug.

14. A closure assembly as recited in claim 10 further comprising at least one frangible connector disposed in removable, interconnecting relation between an interior surface of said housing and an exterior surface of said indicator member.

15. A closure assembly as recited in claim 14 wherein said indicator member is detachable from said housing and retained in surrounding relation to said flow restrictor upon a predetermined axial force being applied to said housing.

16. A closure assembly as recited in claim 15 wherein said predetermined axial force is sufficient to remove said housing from an interconnecting relation to said female connector.

17. A closure assembly as recited in claim 10 wherein said flow restrictor includes a casing having an exterior structure at least partially defined by a plurality of curved segments and a plurality of flat segments, each of said flat segments disposed between and adjacent to two of said plurality of curved segments.

18. A closure assembly structured to indicate attempted access, said closure assembly comprising:
- a female connector associated with an apparatus for administering intravenous fluids to a patient and including an interior port,
- a housing including an at least partially hollow interior and a closed end portion,
- a flow restrictor movably disposed within said housing and structured for connection to said female connector,
- said flow restrictor including a male plug member dimensioned and configured for insertion in flow restricting engagement within said interior port of said female connector,
- said flow restrictor further including a casing having an interior surface disposed in surrounding, spaced relation to said plug member;
- said interior surface cooperatively structured with an exterior of the female connector to establish a connection therebetween,
- said flow restrictor and housing cooperatively structured for concurrent rotational and axial movement of said male plug into said inserted, flow restricting engagement with said female connector.

* * * * *